US011000571B2

(12) United States Patent
Bienkiewicz

(10) Patent No.: US 11,000,571 B2
(45) Date of Patent: May 11, 2021

(54) MODIFIED FRAGMENTS FROM THE OCTAREPEAT REGION OF PRION PROTEIN AS HEMIN BINDERS

(71) Applicant: Florida State University Research Foundation, Inc., Tallahassee, FL (US)

(72) Inventor: Ewa Anna Bienkiewicz, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 37 days.

(21) Appl. No.: 15/632,638

(22) Filed: Jun. 26, 2017

(65) Prior Publication Data

US 2017/0368137 A1    Dec. 28, 2017

Related U.S. Application Data

(60) Provisional application No. 62/354,957, filed on Jun. 27, 2016.

(51) Int. Cl.
*A61K 38/17* (2006.01)

(52) U.S. Cl.
CPC .................................. *A61K 38/177* (2013.01)

(58) Field of Classification Search
USPC .......................................................... 435/7.1
IPC .................................................... A61K 38/177
See application file for complete search history.

(56) References Cited

U.S. PATENT DOCUMENTS

| 7,439,041 | B2 | 10/2008 | Michelitsch et al. | |
|---|---|---|---|---|
| 8,481,482 | B1 * | 7/2013 | Bienkiewicz | A61K 38/16 514/13.5 |
| 8,993,514 | B1 * | 3/2015 | Bienkiewicz | A61K 38/10 514/2.1 |
| 2012/0208763 | A1 | 8/2012 | Gozes | |

FOREIGN PATENT DOCUMENTS

| EP | 1653844 B1 * | 12/2012 | .............. C07K 14/47 |
|---|---|---|---|
| WO | 2011119340 A1 | 9/2011 | |

OTHER PUBLICATIONS

London (Testing for cis' proline with α-aminoisobutyric acid substitution, Int. J. Peptide Protein Res. 1982, 19:334-342) (Year: 1982).*
Ghosh (Phased Fiber Growth in a Peptide Conjugate: Aggregation and Disaggregation Studies, J. Phys. Chem. B 2007, 111:3750-3757) (Year: 2007).*
Bonomo (Copper(II) Binding Modes in the Prion Octapeptide PHGGGWGQ:A Spectroscopic and Voltammetric Study, Chem. Eur. J. 2000, 6) (Year: 2000).*
International Search Report dated Oct. 27, 2017 for PCT/US2017/039210.
Pike et al.; "Conformational Analysis of Helical Aminoisobutyric Acid (Aib) Oligomers Bearing C-Terminal Ester Schellman Motifs"; Organic & Biomolecular Chemistry; vol. 12, Issue 24; pp. 4124-4131; Jun. 28, 2014.
Taubner et al.; "Structure of the Flexible Amino Terminal Domain of Prion Protein Bound to a Sulfated Glycan"; J. Mol Biol.; vol. 395; Issue 3; pp. 474-490; Jan. 22, 2010.
Aravinda et al.; "Aib Residues in Peptaibiotics and Synthetic Sequences: Analysis of Nonhelical Conformations"; Chemistry & Biodiversity; vol. 5; pp. 1238-1262; 2008.
Martin-Quiros et al.; "Absence of a Stable Secondary Structure is Not a Limitation for Photoswitchable Inhibitors of 3-Arrestin/β-Adaptin 2 Protien-Protein-Protein Interaction"; Chemistry & Biology vol. 22; pp. 31-37; Jan. 22, 2015.
Prasad et al.; "The Stereochemistry of Peptides Containing α-Aminoisobutyric Acid"; CRC Critical Reviews in Biochemistry; Vpl. 16, Issue 4; pp. 307-348; 2014.
Prasad et al; "The Stereochemistry of Peptides Containing Alpha-Aminoisobutyric Acid"; CRC Crit Rev. Biochem; vol. 16(4); pp. 307-348; 1984.

* cited by examiner

*Primary Examiner* — Maury A Audet
(74) *Attorney, Agent, or Firm* — Christopher M. Ramsey; GrayRobinson, P.A.

(57) ABSTRACT

An example of the composition incudes at least one amino acid sequence from the octarepeat region of hemin that is modified by substituting at least one proline (P) residue in the amino acid sequence. The composition is effective to bind with hemin and for treating hemorrhagic injury.

13 Claims, 7 Drawing Sheets
Specification includes a Sequence Listing.

|   | 0 | 1 | 2 | 3 | 4 |
|---|---|---|---|---|---|
| (1) Body symmetry (open bench top) | Normal | Slight asymmetry | Moderate asymmetry | Prominent asymmetry | Extreme asymmetry |
| (2) Gait (open bench top) | Normal | Stiff, inflexible | Limping | Trembling, drifting, falling | Does not walk |
| (3) Climbing (gripping surface, 45° angle) | Normal | Climbs with strain, limb weakness pre- | Holds onto slope, does not slip or climb | Slides down slope, unsuccessful effort to prevent fall | Slides immediately, no effort to prevent fall |
| (4) Circling behavior (open bench top) | Not present | Predominantly one-sided turns | Circles to one side (not constantly) | Circles constantly to one side | Pivoting, swaying, or no movement |
| (5) Front limb symmetry (mouse suspended by its tail) | Normal | Light asymmetry | Marked asymmetry | Prominent asymmetry | Slight asymmetry, no body/limb movement |
| (6) Compulsory circling (front limbs on bench, rear suspended by tail) | Not present | Tendency to turn to one side | Circles to one side | Pivots to one side sluggishly | Does not advance |
| (7) Whisker response (light touch from behind) | Symmetrical response | Light asymmetry | Prominent asymmetry | Absent response ipsilaterally, diminished contralaterally | Absent proprioceptive response bilaterally |

*FIG. 4*

 sham

 saline

 16 mg/kg SEQ ID NO: 3

 16 mg/kg Aib modified SEQ ID NO: 3

 32 mg/kg SEQ ID NO: 3

 32 mg/kg Aib modified SEQ ID NO: 3 a → $p < 0.05$ b → $p < 0.01$ c → $p < 0.001$ d → $p < 0.0001$

*FIG. 5*

SEQUENCE LISTING

```
<160> NUMBER OF SEQ ID NOS: 11

<210> SEQ ID NO 1
<211> LENGTH: 252
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Thr His Ser
                85                  90                  95

Gln Trp Asn Lys Pro Ser Lys Pro Lys Thr Asn Met Lys His Met Ala
            100                 105                 110

Gly Ala Ala Ala Gly Ala Val Val Gly Gly Leu Gly Gly Tyr Met
        115                 120                 125

Leu Gly Ser Ala Met Ser Arg Pro Ile Ile His Phe Gly Ser Asp Tyr
    130                 135                 140

Glu Asp Arg Tyr Tyr Arg Glu Asn Met His Arg Tyr Pro Asn Gln Val
145                 150                 155                 160

Tyr Tyr Arg Pro Met Asp Glu Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Ile Thr Gln Tyr Glu Arg Glu Ser Gln Ala Tyr
    210                 215                 220

Tyr Gln Arg Gly Ser Ser Met Val Leu Phe Ser Ser Pro Pro Val Ile
225                 230                 235                 240
```

```
Leu Leu Ile Ser Phe Leu Ile Phe Leu Ile Val Gly
            245                 250

<210> SEQ ID NO 2
<211> LENGTH: 8
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 2

Pro His Gly Gly Gly Trp Gly Gln
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 3

Pro His Gly Gly Gly Trp Gly Gln Pro His Gly Gly Gly Trp Gly Gln
1               5                   10                  15

<210> SEQ ID NO 4
<211> LENGTH: 24
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 4

Pro His Gly Gly Gly Trp Gly Gln Pro His Gly Gly Gly Trp Gly Gln
1               5                   10                  15

Pro His Gly Gly Gly Trp Gly Gln
            20

<210> SEQ ID NO 5
<211> LENGTH: 32
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 5

Pro His Gly Gly Gly Trp Gly Gln Pro His Gly Gly Gly Trp Gly Gln
1               5                   10                  15

Pro His Gly Gly Gly Trp Gly Gln Pro His Gly Gly Gly Trp Gly Gln
            20                  25                  30

<210> SEQ ID NO 6
<211> LENGTH: 37
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 6

Gly Gln Pro His Gly Gly Gly Trp Gly Gln Pro His Gly Gly Gly Trp
1               5                   10                  15

Gly Gln Pro His Gly Gly Gly Trp Gly Gln Pro His Gly Gly Gly Trp
            20                  25                  30

Gly Gln Gly Gly Gly
```

```
<210> SEQ ID NO 7
<211> LENGTH: 8
<212> TYPE: PRT
<213> ORGANISM: Artificial Sequence
<220> FEATURE:
<223> OTHER INFORMATION: SYNTHETICALLY GENERATED PEPTIDE
<220> FEATURE:
<221> NAME/KEY: MISC_FEATURE
<222> LOCATION: (1)..(8)
<223> OTHER INFORMATION: X = 2-AMINOISOBUTYRIC ACID

<400> SEQUENCE: 7

Xaa His Gly Gly Gly Trp Gly Gln
1               5

<210> SEQ ID NO 8
<211> LENGTH: 16
<212> TYPE: PRT
<213> ORGANISM: Artificial Sequence
<220> FEATURE:
<223> OTHER INFORMATION: SYNTHETICALLY GENERATED PEPTIDE
<220> FEATURE:
<221> NAME/KEY: MISC_FEATURE
<222> LOCATION: (1)..(16)
<223> OTHER INFORMATION: X = 2-AMINOISOBUTYRIC ACID

<400> SEQUENCE: 8

Xaa His Gly Gly Gly Trp Gly Gln Xaa His Gly Gly Gly Trp Gly Gln
1               5                   10                  15

<210> SEQ ID NO 9
<211> LENGTH: 24
<212> TYPE: PRT
<213> ORGANISM: Artificial Sequence
<220> FEATURE:
<223> OTHER INFORMATION: SYNTHETICALLY GENERATED PEPTIDE
<220> FEATURE:
<221> NAME/KEY: MISC_FEATURE
<222> LOCATION: (1)..(24)
<223> OTHER INFORMATION: X = 2-AMINOISOBUTYRIC ACID

<400> SEQUENCE: 9

Xaa His Gly Gly Gly Trp Gly Gln Xaa His Gly Gly Gly Trp Gly Gln
1               5                   10                  15

Xaa His Gly Gly Gly Trp Gly Gln
                20

<210> SEQ ID NO 10
<211> LENGTH: 32
<212> TYPE: PRT
<213> ORGANISM: Artificial Sequence
<220> FEATURE:
<223> OTHER INFORMATION: SYNTHETICALLY GENERATED PEPTIDE
<220> FEATURE:
<221> NAME/KEY: MISC_FEATURE
<222> LOCATION: (1)..(32)
<223> OTHER INFORMATION: X = 2-AMINOISOBUTYRIC ACID

<400> SEQUENCE: 10

Xaa His Gly Gly Gly Trp Gly Gln Xaa His Gly Gly Gly Trp Gly Gln
1               5                   10                  15

Xaa His Gly Gly Gly Trp Gly Gln Xaa His Gly Gly Gly Trp Gly Gln
                20                  25                  30

<210> SEQ ID NO 11
<211> LENGTH: 37
```

```
<212> TYPE: PRT
<213> ORGANISM: Artificial Sequence
<220> FEATURE:
<223> OTHER INFORMATION: SYNTHETICALLY GERATED PEPTIDE
<220> FEATURE:
<221> NAME/KEY: MISC_FEATURE
<222> LOCATION: (1)..(37)
<223> OTHER INFORMATION: X = 2-AMINOISOBUTYRIC ACID

<400> SEQUENCE: 11

Gly Gln Xaa His Gly Gly Gly Trp Gly Gln Xaa His Gly Gly Gly Trp
1               5                   10                  15

Gly Gln Xaa His Gly Gly Gly Trp Gly Gln Xaa His Gly Gly Gly Trp
            20                  25                  30

Gly Gln Gly Gly Gly
        35
```

MODIFIED FRAGMENTS FROM THE OCTAREPEAT REGION OF PRION PROTEIN AS HEMIN BINDERS

CROSS-REFERENCE TO RELATED APPLICATION

This claims priority from U.S. provisional Application No. 62/354,957, filed Jun. 27, 2016, the entire contents of which are incorporated by reference.

FIELD

This relates to the field of peptide-hemin interactions and, more particularly, to using modified amino acid sequences found in prion protein to bind hemin.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. § 1.821(c) and the computer readable file required by 37 C.F.R. § 1.821(c). The information contained in the Sequence Listing is incorporated herein by reference in its entirety.

BACKGROUND

The prion protein, PrP for short, is found throughout the body of humans and other animals. PrP exists in two forms. The normal endogenous form of PrP, called $PrP^C$ or cellular PrP, is non-infectious. In contrast, the second form of PrP, called $PrP^{SC}$, is infectious. The difference is primarily attributable to the fact that the molecular structure of $PrP^{SC}$ is mis-folded relative to that of $PrP^C$.

$PrP^{SC}$ is responsible for causing prion diseases, including transmissible spongiform encephalopathies such as mad cow disease and Creutzfeldt-Jakob disease. $PrP^{SC}$ is also responsible for generating amyloid fibrils in neural tissue, which can result in irreversible neurodegeneration.

$PrP^C$, on the other hand, appears to be involved in numerous cellular functions, including signal transduction, neuroprotection, and angiogenesis.

Heme is an iron containing component of hemoproteins such as hemoglobin and is an essential component of oxygen transport. Hemin, a derivative of heme, is produced by the body and is released in a vascular injury event such as a stroke.

Hemin toxicity is a source of brain damage following hemorrhagic stroke. Hemorrhagic stroke involves the rupture of an intracerebral artery, which subsequently results in a hematoma caused by the pooling of blood. This prevents the cells from receiving oxygen and vital nutrients, causing the cells to die. In ischemic stroke, hypoxia damages vasculature, resulting in microbleeds. After the acute brain injury caused by the stroke, brain damage can continue to occur over the following days and weeks. This has been attributed to the presence of hemin at the site of the hematoma (Robinson, et al, "Hemin toxicity: a preventable source of brain damage following hemorrhagic stroke." *Redox Report*, Vol. 14, No. 6 (2009)). According to Robinson, et al., elevated levels of hemin can be toxic, causing tissue injury and even death.

Blood contains about 2.5 mM of hemoglobin, which, when broken down can yield 10 mM of hemin. Cell culture experiments suggest that as little as 3-30 μM of hemin is sufficient to kill 60%-70% of cultured neurons and astrocytes within 4-14 hours.

SUMMARY

Because hemin is toxic, it would be useful to have a composition that could bind to hemin. An example of such a composition includes at least one isolated amino acid sequence selected from SEQ ID NOs: 2, 3, 4, 5, and 6 in which at least one proline (P) residue in the amino acid sequence is substituted by an amino acid having the formula $$H_2N-\underset{\underset{R_1\ R_2}{|}}{C}-C(=O)-OH.$$

An example of a method of binding hemin includes administering to a hemin solution a composition comprising at least one isolated amino acid sequence selected from SEQ ID NOs: 2, 3, 4, 5, and 6 in which at least one proline (P) residue in the amino acid sequence is substituted by an amino acid having the formula $$H_2N-\underset{\underset{R_1\ R_2}{|}}{C}-C(=O)-OH,$$

wherein the isolated amino acid sequence is effective for binding to hemin in the hemin solution.

An example of a method of treating a hemorrhagic injury includes administering to a patient in need thereof a therapeutically effective composition comprising at least one isolated amino acid sequence selected from SEQ ID NOs: 2, 3, 4, 5, and 6 in which at least one proline (P) residue in the amino acid sequence is substituted by an amino acid having the formula $$H_2N-\underset{\underset{R_1\ R_2}{|}}{C}-C(=O)-OH.$$

The following may be additional features of the composition and/or methods.

The formula may include a butyric acid group.

R1 and R2 may be alkyl functional groups having 1 to 4 carbon atoms.

R1 and R2 may be independently selected from methyl, ethyl, butyl, and propyl groups.

R1 and R2 may be methyl groups.

The composition may be within a pharmaceutical dosage form.

The isolated amino acid sequence is effective for binding to hemin.

BRIEF DESCRIPTION OF THE DRAWINGS

FIG. 4 is a table of the components of the 28 point scale and the corresponding scoring criteria.

FIG. 5 is a legend for the bar graphs of FIGS. 6-12.

In FIGS. 6-12, a higher score means more significant deficit. Data were analyzed using two-way ANOVA, relative to saline, with Bonferroni correction. Graphs show the mean±SEM and statistical significance, where a is p<0.05, b is p<0.01, c is p<0.001, and d is p<0.0001.

DETAILED DESCRIPTION OF EXAMPLE EMBODIMENTS

As used herein, the following terms have the following meanings. Both the singular and plural forms of a term are included, regardless of the form discussed in this section.

"Prion," prion protein," and "PrP" are used interchangeably to refer to both the pathogenic prion protein form ("PrP$^{SC}$") and the non-pathogenic prion protein form ("PrP$^C$"). Use of "prion," prion protein," and "PrP" is not meant to be limited to the polypeptides having the exact sequences as those described herein.

"PrP$^C$" means the native prion protein, which is naturally expressed in Mammalia.

"PrP$^{SC}$" means the structurally altered form of PrP$^C$ that is considered to be pathogenic.

"Ischemic stroke" means a stroke caused by blockage of blood supply. Typical blockages are caused by a thrombus or embolus.

"Hemorrhagic stroke" means a stroke involving the rupture of an artery and subsequent hematoma.

Figure 1:
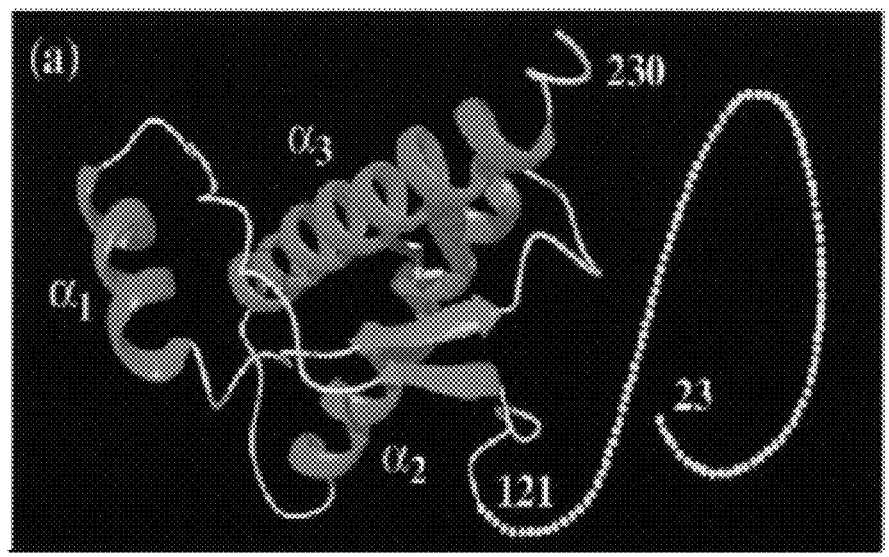
FIG. 1 is a diagram of the molecular structure of $PrP^C$ from residues 23-230 as determined by NMR data.

FIG. 1 is a diagram of the structure of PrP$^C$ from residues 23-231. It includes a plurality of α-helix regions and β pleated-sheet regions. The C-terminal domain is structurally ordered while the N-terminal domain is referred to as being "flexibly disordered." To provide a better understanding, this structure has been simplified into the simple schematic of FIG. 2. The portion of the sequence beginning with residue 23 is called the N-terminal domain. The opposite end is called the C-terminal domain. The relative locations of the α-helix regions and β pleated-sheet regions are indicated, respectively, by the α and β symbols.

The human amino acid sequence of a full length human PrP$^C$ is provided in TABLE 1. A section of the sequence called the "ocatarepeat region" or "OR region" is bolded.

TABLE 1

Amino acid sequence of human PrP$^C$

| SEQ ID NO: | Sequence |
|---|---|
| 1 | MANLGCWMLVLFVATWSDLGLCKKRPKPGGWNTGGSRYPGQGSPG GNRYPPQGGGGWGQPHGGGWGQPHGGGWGQPHGGGWGQPHGGGWG QGGTHSQWNKPSKPKTNMKHMAGAAAAGAVVGGLGGYMLGSAMSR PIIHFGSDYEDRYYRENMHRYPNQVYYRPMDEYSNQNNFVHDCVN ITIKQHTVITTTKGENFTETDVKKMERVVEQMCITQYERESQAYY QRGSSMVLFSSPPVILLISFLIFLIVG |

Figure 2:
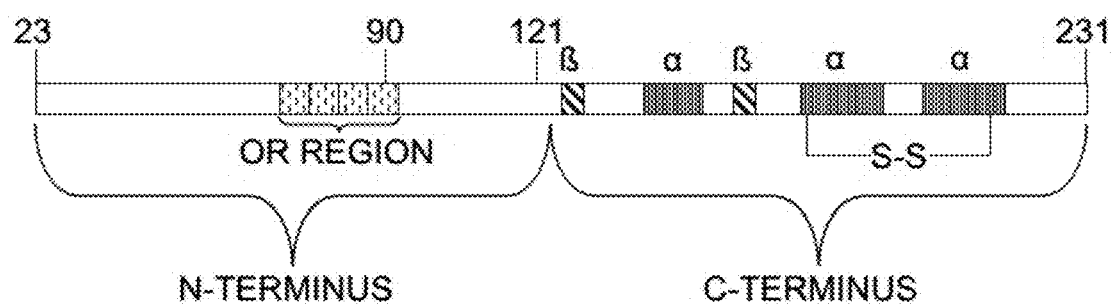
FIG. 2 is a schematic of the structure of PrP$^C$, highlighting certain features of the structure.

The octarepeat region contains a sequence of eight amino acid residues, an octamer that repeats four times. The location of the OR region in the N-terminal domain is indicated in FIG. 2.

TABLE 2 provides the amino acid sequences corresponding to 1, 2, 3, and 4 repeats and their corresponding SEQ ID NOs. SEQ ID NO: 5, includes the 4-repeat fragment of SEQ ID NO: 4, but also includes the bolded residues. When isolated, SEQ ID NOs: 2-6 adopt a modular structure.

TABLE 2

Amino acid sequences of the 1-, 2-, 3-, and 4-repeat peptides of the octarepeat region

| #Repeats | SEQ ID NO: | Sequence |
|---|---|---|
| 1 | 2 | PHGGGWGQ |
| 2 | 3 | PHGGGWGQPHGGGWGQ |
| 3 | 4 | PHGGGWGQPHGGGWGQPHGGGWGQ |
| 4 | 5 | PHGGGWGQPHGGGWGQPHGGGWGQPHGGGWGQ |
| 4 | 6 | GQPHGGGWGQPHGGGWGQPHGGGWGQPHGGGW GQGGG |

The octarepeat region contains a sequence of eight amino acid residues, an octamer, that repeats four times. The location of the OR region in the N-terminal domain is indicated in FIG. 2. TABLE 2 provides the amino acid sequences corresponding to 1, 2, 3, and 4 repeats and their corresponding SEQ ID NOs. SEQ ID NO: 5, includes the 4-repeat fragment of SEQ ID NO: 4, but also includes the underlined residues. When isolated, SEQ ID NOs: 2-6 adopt a modular structure.

U.S. Pat. Nos. 8,993,514 and 8,481,482 show that that isolated portions of the N-terminal domain chemically bind to hemin molecules, which makes those portions a therapeutic agent for preventing vascular injury caused by hemin after a vascular injury causing event. In particular, it was shown that isolated fragments of the N-terminal domain that include SEQ ID NOs: 2, 3, 4, 5, 6 or combinations thereof are effective for binding hemin.

Figure 3:
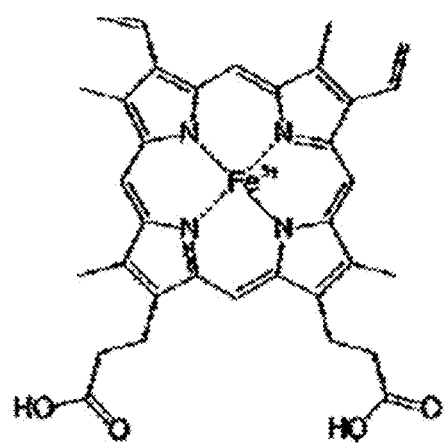
FIG. 3 is a diagram of a hemin molecule.

The structure of hemin is shown in FIG. 3. Hemin is a Fe(3+)containing porphyrin molecule in which the Fe(3+) ion is coordinated to the four N atoms of the porphyrin ligand.

2-aminoisobutyric acid ("Aib") is an amino acid with the formula shown below.
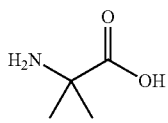

Without intending to be bound by theory, it is believed that substituting at least one proline (P) residue in SEQ ID Nos: 2, 3, 4, 5, or 6 with Aib or a derivative thereof stabilizes the respective sequence, causing the modified sequence to bind hemin stronger than the unmodified sequence. This modification may make the modified sequences better hemin binders with improved therapeutic efficacy compared to the unmodified sequences.

Table 3 provides a sequence listing for Aib-modified SEQ ID Nos: 2-6 where the proline residues have been substituted with Aib.

TABLE 3

Modified amino acid sequences of the 1-, 2-, 3-, and 4- repeat peptides of the octarepeat region

| #Repeats | SEQ ID NO: | Modified Sequence |
|---|---|---|
| 1 | 7 | (Aib)HGGGWGQ |
| 2 | 8 | (Aib)HGGGWGQ(Aib)HGGGWGQ |
| 3 | 9 | (Aib)HGGGWGQ(Aib)HGGGWGQ(Aib) HGGGWGQ |
| 4 | 10 | (Aib)HGGGWGQ(Aib)HGGGWGQ(Aib) HGGGWGQ(Aib)HGGGWGQ |
| 4 | 11 | GQ(Aib)HGGGWGQ(Aib)HGGGWGQ(Aib) HGGGWGQ(Aib)HGGGWGQGGG |

Aib and its derivatives may be used as the substitute amino acid. Derivatives of Aib may have the formula shown in Compound 1.

Compound 1

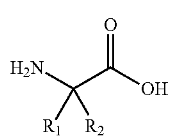

The abbreviations used in Compound 1 are those typically used in organic chemical synthesis. R1 and R2 represent generic functional groups. They may be the same or they may be different, depending on the version of Compound 1 that is desired. When R1 and R2 are both methyl ($CH_3$) groups, Compound 1 is Aib.

The primary limitation for the identity of R1 and R2 is that together, they should not result in destabilizing the sequence's conformation. It is believed that Aib stabilizes the turn conformation.

Examples of functional groups from which R1 and R2 may be independently selected include, but are not limited to, non-polar, small alkyl functional groups having 1-4 carbon atoms, such as methyl, ethyl, butyl, and propyl groups among many other possible examples.

A composition embodying these principles includes at least one isolated amino acid sequence selected from SEQ ID NOs: 2, 3, 4, 5, and 6 in which at least one proline (P) residue in the amino acid sequence is substituted by an amino acid having the formula of Compound 1.

The composition may be used to treating the toxic effects of hemin to vascular and neural tissue, which occur as a result of a condition involving cellularly toxic hemin levels, such as a hemorrhagic stroke, ischemic stroke, or traumatic brain injury (TBI) for example.

Such a method of treating a hemorrhagic injury includes administering a composition including at least one isolated amino acid sequence selected from SEQ ID NOs: 2, 3, 4, 5, and 6 in which at least one proline (P) residue in said amino acid sequence is substituted by an amino acid having the formula of Compound 1.

Such a method of treating a condition characterized by cellularly toxic hemin levels includes administering a composition including at least one isolated amino acid sequence selected from SEQ ID NOs: 2, 3, 4, 5, and 6 in which at least one proline (P) residue in said amino acid sequence is substituted by an amino acid having the formula of Compound 1.

A method of binding hemin includes administering a composition including at least one isolated amino acid sequence selected from SEQ ID NOs: 2, 3, 4, 5, and 6 in which at least one proline (P) residue in said amino acid sequence is substituted by an amino acid having the formula of Compound 1 to a solution containing hemin, wherein the isolated amino acid sequence is effective for forming one or more chemical bonds with hemin. In this embodiment, suitable solutions include in vitro and in vivo solutions such as in vitro or in vivo blood solutions, plasma solutions, or hemin containing solutions, for example.

In these embodiments, the isolated amino acid sequences, fragments thereof, variants thereof, or homologues thereof may be used to bind hemin. Embodiments of the composition and methods may include one or more combinations of the amino acid sequences, one or more combinations of fragments thereof, one or more combinations of variants thereof, and/or one or more combinations of homologues thereof. The term "isolated" in this case, means that the modified amino acid sequence, fragment, variant, or homologue is present separately from the native $PrP^C$ protein.

A fragment is an amino acid sequence which has at least 40%, more preferably at least 50%, more preferably at least 60%, more preferably at least 70%, more preferably at least 80%, more preferably at least 90%, more preferably at least 95% of SEQ ID NOs: 2, 3, 4, 5, or 6 in which at least one proline (P) residue in the amino acid sequence is substituted by an amino acid having the formula of Compound 1.

A variant is an amino acid sequence having at least 60%, more preferably at least 70%, more preferably at least 80%, more preferably at least 90%, more preferably 95% homology to SEQ ID NOs: 2, 3, 4, 5, or 6 in which at least one proline (P) residue in the amino acid sequence is substituted by an amino acid having the formula of Compound 1. A variant may also be an amino acid sequence having at least 60%, more preferably at least 70%, more preferably at least 80%, more preferably at least 90%, more preferably 95% positive amino acid matches compared to a sequence SEQ ID NOs: SEQ ID NOs: 2, 3, 4, 5, or 6 in which at least one proline (P) residue in the amino acid sequence is substituted by an amino acid having the formula of Compound 1.

A positive amino acid match has an identity or similarity defined by physical and/or chemical properties of the amino acids having the same position in two compared sequences. The homology of the sequences may be calculated using conventional algorithms.

A homologue is an amino acid sequence which has less than 60% but more than 30%, such as 50-59%, for example 55%, such as 40-49%, for example 45%, such as 30-39%, for example 35% homology to a sequence comprising SEQ ID NOs: SEQ ID NOs: 2, 3, 4, 5, or 6 in which at least one proline (P) residue in the amino acid sequence is substituted by an amino acid having the formula of Compound 1.

Exemplary conditions involving cellularly toxic hemin levels include, but are not limited to, vascular injury conditions such as hemorrhagic stroke, ischemic stroke, traumatic brain injury or other traumatic injury, bleeding wounds, reperfusion, hemophilia, and sickle cell anemia. A cellularly toxic hemin level is a concentration of hemin that is sufficient to kill the cells to which hemin is administered. A cellularly toxic hemin level may be, for example, about 3 μM to about 30 μM of hemin.

Aside from the one or more modified isolated amino acid sequences, the composition may also include one or more ingredients useful for making the composition into a pharmaceutically acceptable dosage form such as a suspension, tablet, capsule, injectable, or the like that can be administered to a human or animal patient. Exemplary ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, antiadherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

The composition may be administered to a subject by way of, for example, contacting the subject with the composition, injecting the subject with the composition, ingesting the composition, or the like. Subjects include, but are not limited to humans, animals, cells, and solutions containing hemin, including in vitro and in vivo solutions.

The N-terminus of the amino acid sequence that is administered may be acetylated and the C-terminus of the amino acid sequence that is administered may be amidated. This may be useful for stabilizing the amino acid sequences when they are isolated. Acetylation and amidation of the amino acid sequences may be achieved using conventional biochemical techniques.

The number of hemin molecules bound by the amino acid sequence administered may be a function of the pH. During stroke or stroke-like conditions, the plasma pH decreases from the normal physiological pH of about 7.4. The binding capacity of the amino acid sequence administered may increase as the pH decreases. Accordingly, the amino acid sequence(s) administered may serve as high-capacity hemin binders during stroke or stroke-like conditions, or any bleeding events that result in release of toxic levels of hemin. Accordingly, the methods may include administering the isolated amino acid sequence(s) when the solution that contains hemin has a pH below 7.4.

EXAMPLES

This section discusses experimental examples. The scope of possible embodiments is not limited only to the details presented in these examples.

Synthesis of Modified SEQ ID NO: 3

This section provides an example of a method for making a modified two-repeat fragment, or Aib modified SEQ ID NO:3, which is SEQ ID No: 8.

Aib modified SEQ ID NO:3 (SEQ ID NO: 8), was synthesized using standard Fmoc-chemistry with 3 eq coupling using HBTU/NMM in DMF. The deprotection was achieved with 20% piperidine/DMF. The peptide was cleaved from resin with TFA/TIS/H2O 95/2.5/2.5. for 2 hr. The crude peptide was purified via reverse-phase HPLC on C18 column with 0-40% B in 60 min. gradient. The buffer A is 0.1% TFA/H2O and buffer B is 0.1% TFA/ACN. The pure fraction was lyophylized to get the final product.

Example 2: Efficacy Testing of Modified SEQ ID NO: 3

An intracerebral hemorrhage ("ICH") mouse model was used to study the efficacy of SEQ ID NO: 8. The mouse model is discussed in Rynkowski, et al., Nature Protocols, Vol. 3, Issue 1, pgs. 122-28 (2008) The ICH was induced by an injection of homologous blood, and the subsequent sequence of events and the efficacy of the tested peptides were evaluated using neurological, behavioral, and molecular tests.

The peptide dose was determined based on pilot studies in using the ICH model (FSU, ACUC protocol #1416), where treatment with 16 mg/kg of SEQ ID NO: 3 administered 1, 4, 24, and 48 hours after ICH induction improved neurofunction. Adult male C57BL/6J mice weighing 23-30 g were randomized into four experimental groups (treatments): (1) 32 mg/kg peptide (in PBS), (2) 16 mg/kg peptide (in PBS), (3) vehicle (PBS, or saline), and (4) sham (no ICH/no treatment). Each group of mice received intraperitoneal (IP) injections of the peptide or an equal volume of PBS. The peptide was administered at 1, 4, 24 and 48 hours after ICH induction in a volume of 150 μL per injection. The sham group of mice were given PBS in the same manner.

Behavioral and Neurofunction Testing

Acute neurological deficits were assessed (and compared to untreated controls) using a 28-point neurological scoring system at 6, 24, 48 and 72 h post-injury.

A 28-point neurological scale was used to measure body symmetry, gait, climbing, circling behavior, front limb symmetry, compulsory circling, and whisker response. Using criteria listed in the table of FIG. 4, each behavior/response was graded from 0 to 4, with a maximum deficit score of 28.

Figure 6:
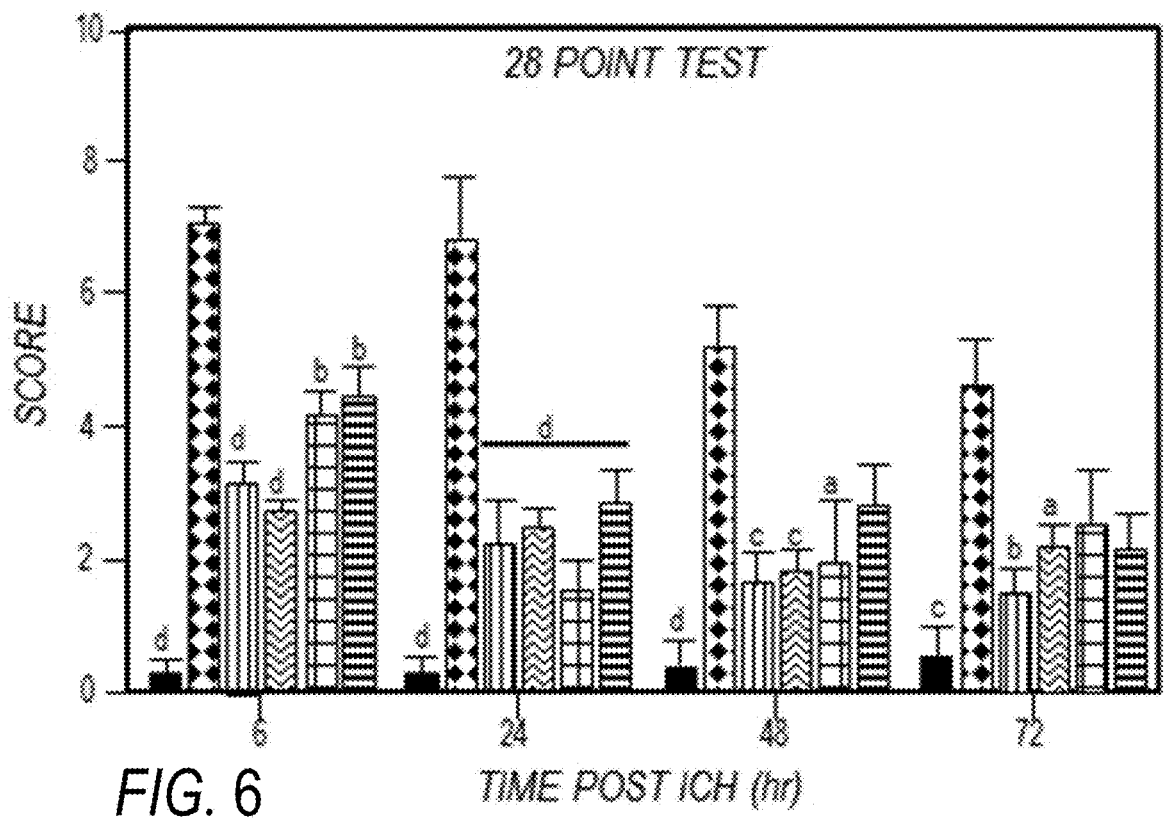
FIG. 6 is a bar graph of the 28 point neurological scale scores at 6, 24, 48, and 72 hours post ICH.
Figure 7:
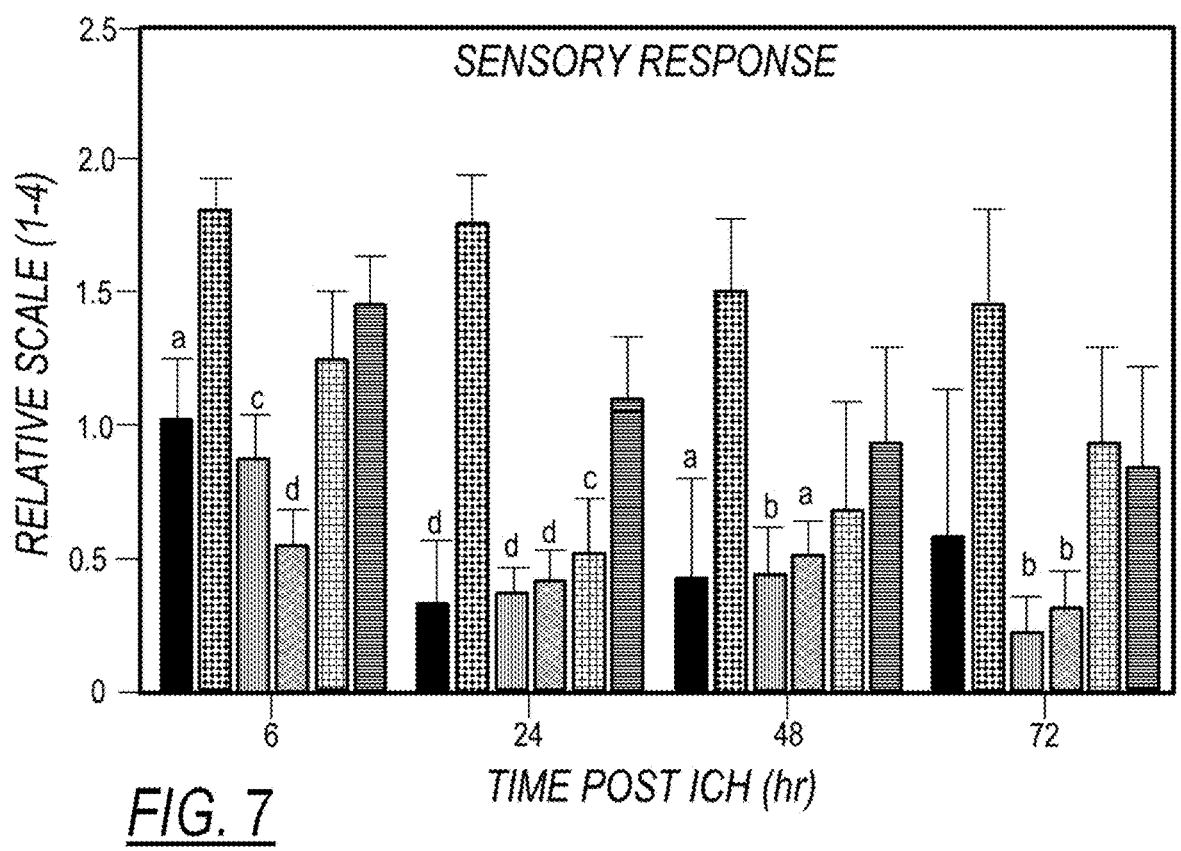
FIG. 7 is a bar graph of the sensory response component of the 28 point neurological scale.
Figure 8:
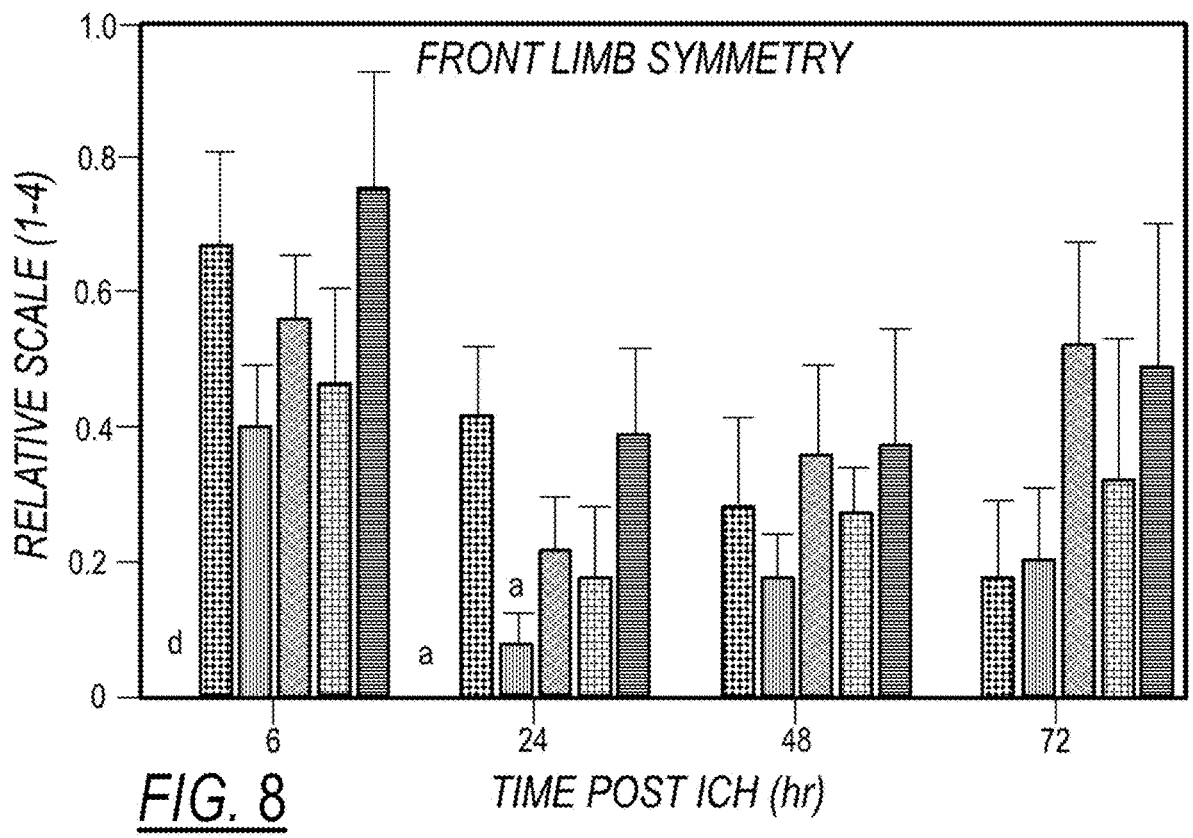
FIG. 8 is a bar graph of the front limb symmetry component of the 28 point neurological scale.
Figure 9:
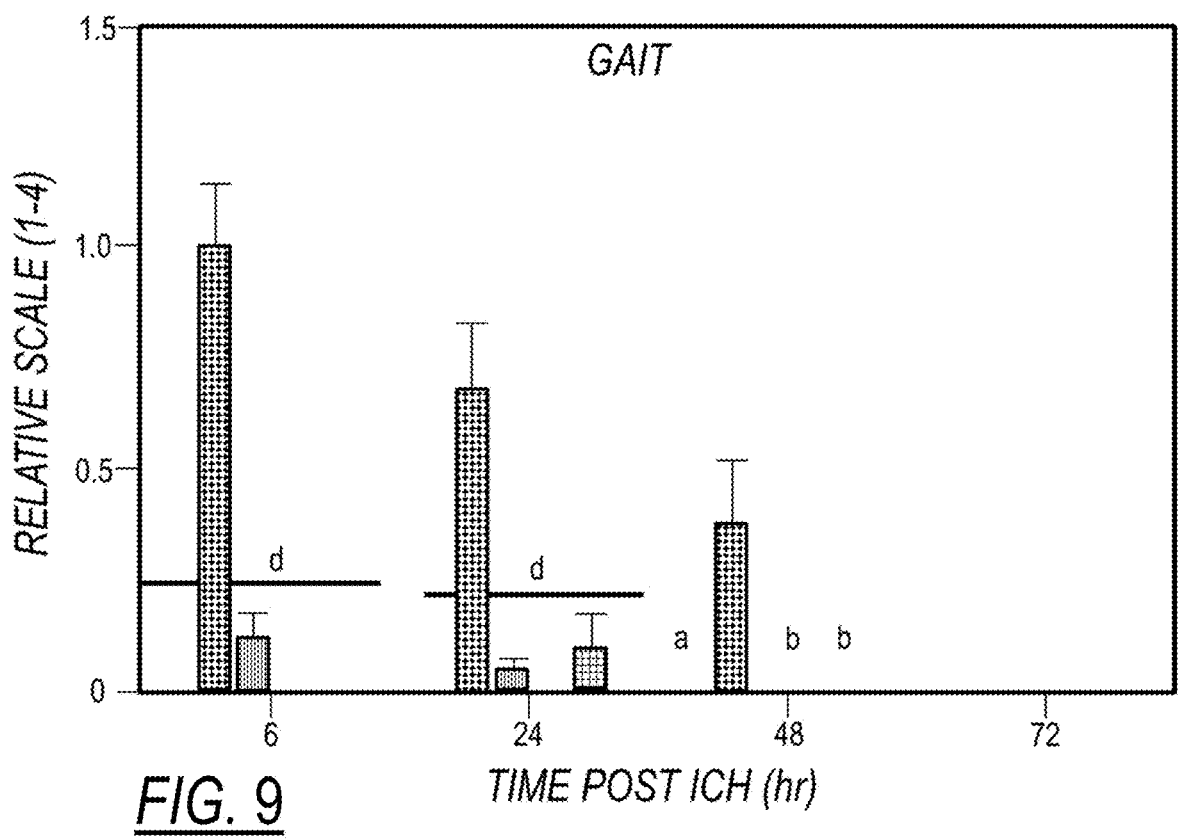
FIG. 9 is a bar graph of the gait component of the 28 point neurological scale.

Treatment with each peptide at either 16 mg/kg or 32 mg/kg dose at 6 and 24 hours post-ICH alleviated behavioral and neurological deficits caused by ICH, as shown in FIG. 6. The 16 mg/kg and 32 mg/kg doses of SEQ ID NO:3 and SEQ ID NO: 8 were effective at each time point tested, as reflected in statistically significant reduction of the 28-point scale score. The only exception was the 32 mg/kg SEQ ID NO:3 and SEQ ID NO: 8 at 72 hours post-ICH, which did not result in statistically significant difference relative to untreated animals. Even in that case, however, the score followed a reduced trend as compared to saline.

The control (sham/no ICH) animals demonstrated a low, statistically significant score throughout all conditions tested. Overall, both SEQ ID NO:3 and SEQ ID NO: 8 appear to be efficacious at diminishing the behavioral and neurological deficits observed in mice following induction of ICH. As expected, the saline (no peptide treatment) ICH animals showed self-recovery over the time course of these experiments.

Examination of the individual 28-point scale components (shown in FIG. 4) revealed sensory and neurological areas where SEQ ID NO: 3 and SEQ ID NO: 8 affected the outcomes, as shown in FIGS. 6-12.

For example, the sensory response (FIG. 7) improved at statistically significant levels by 16 mg/kg for SEQ ID NO:3 and SEQ ID NO: 8 at 6 hrs, by high and low SEQ ID NO:3 and SEQ ID NO: 8 dose, and low SEQ ID NO: 8 dose at 24 hours, and by 16 mg/kg dose of both peptides at 48 and 72 hours.

Gait (FIG. 9) was improved by all peptide treatments at 6 and 24 hour time points, with sham showing natural recovery over time.

Figure 10:
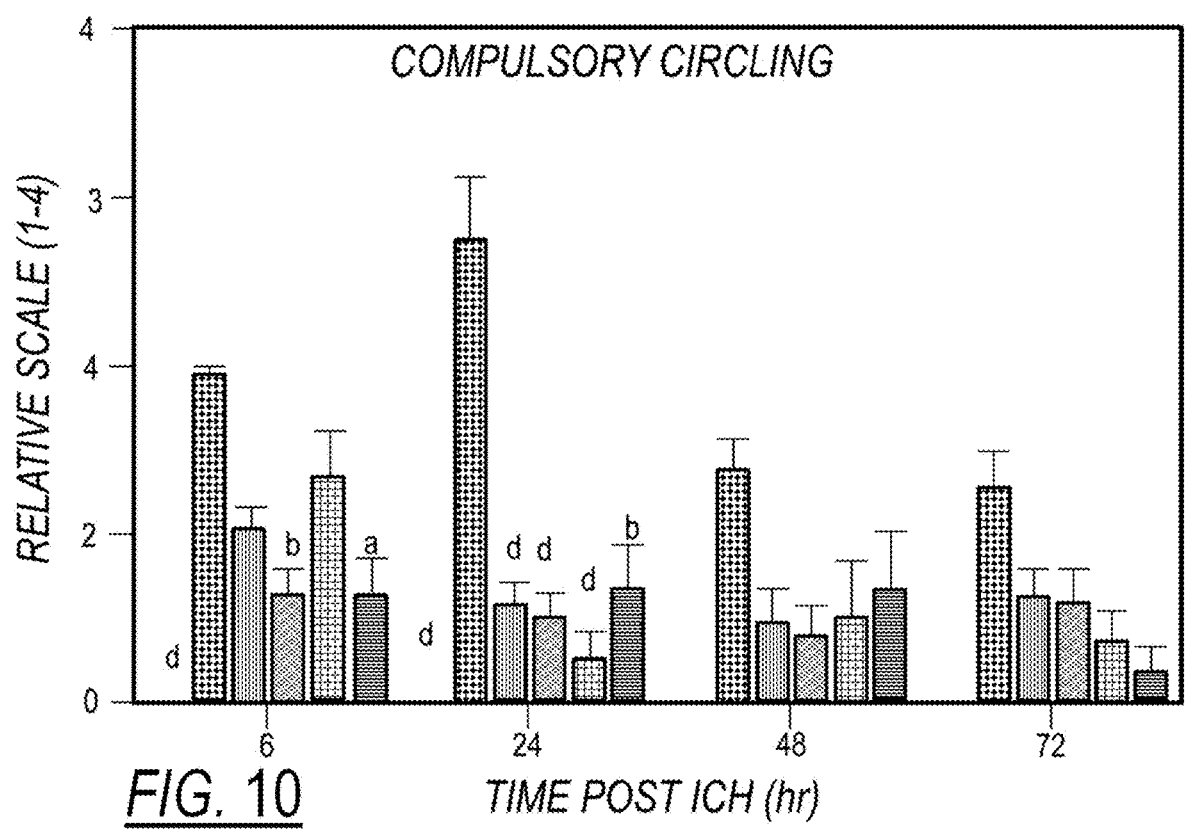
FIG. 10 is a bar graph of the compulsory circling component of the 28 point neurological scale.
Figure 11:
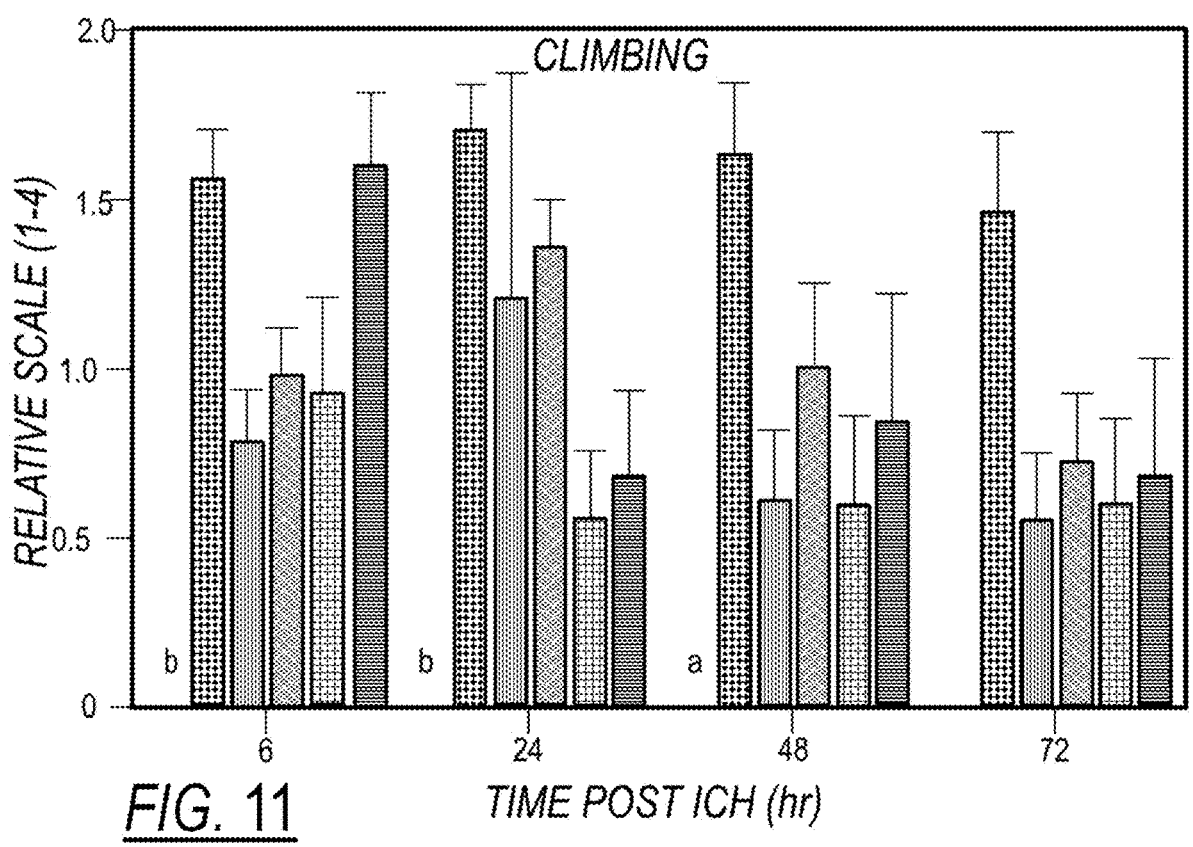
FIG. 11 is a bar graph of the climbing component of the 28 point neurological scale.
Figure 12:
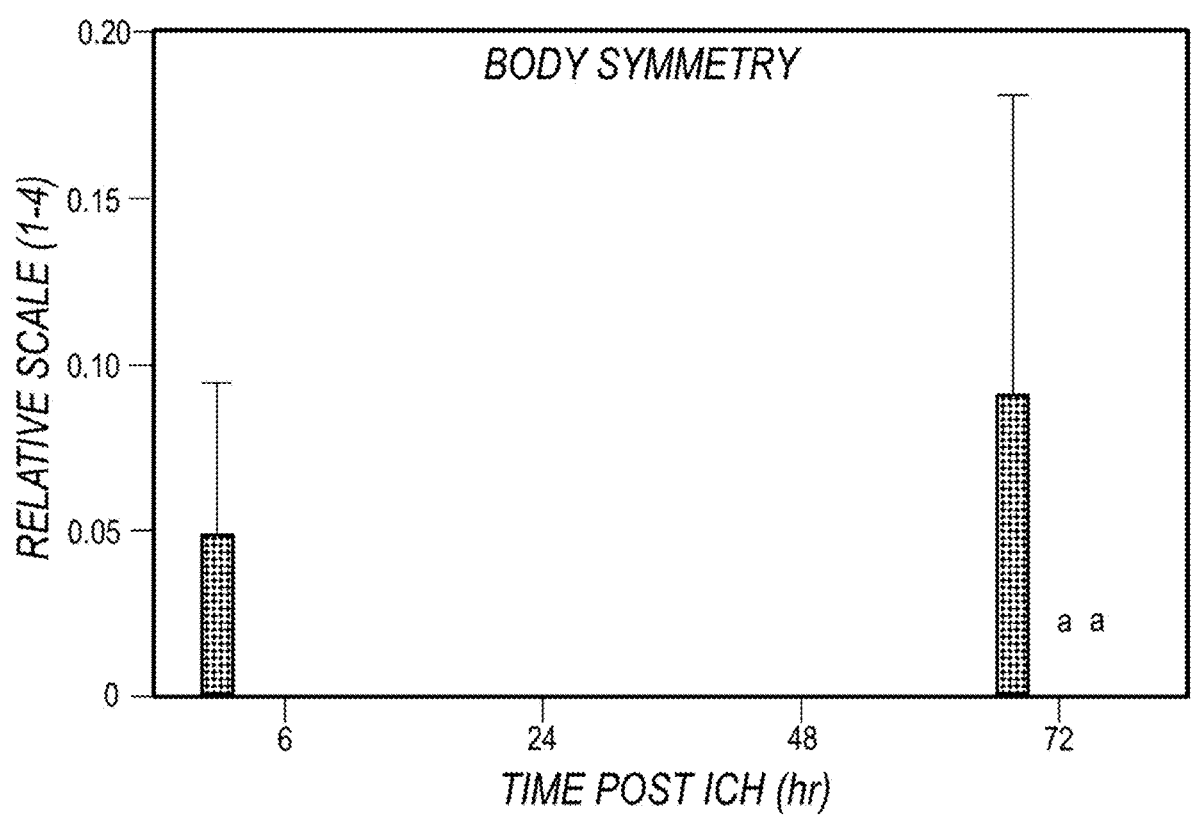
FIG. 12 is a bar graph of the body symmetry component of the 28 point neurological scale.

Compulsory circling (FIG. 10) improved with peptide treatment at all time points (either statistically significant, or strong trend), whereas the climbing score (FIG. 11), body symmetry (FIG. 8), and circling behavior do not appear to be impacted by peptide treatment, with the exception of 32 mg/kg of SEQ ID NO:3 at 6 and 72 hrs circling behavior time (FIG. 10).

Blood Collection and Stroke Biomarker Analysis

Figure 13:
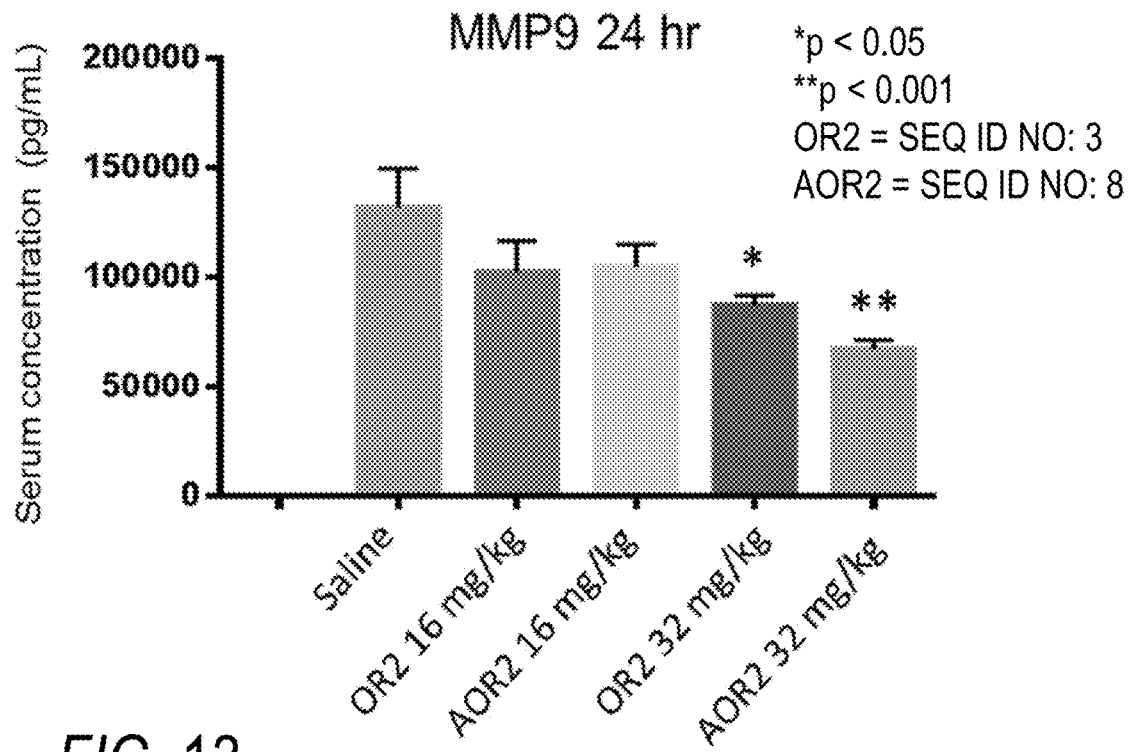
FIG. 13 is a bar graph of the MMP9 serum levels at 24 hours Data were analyzed relative to saline (no peptide) treatment using one-way ANOVA with Dunnett's post-hoc test. *p<0.05, **p<0.001.
Figure 14:
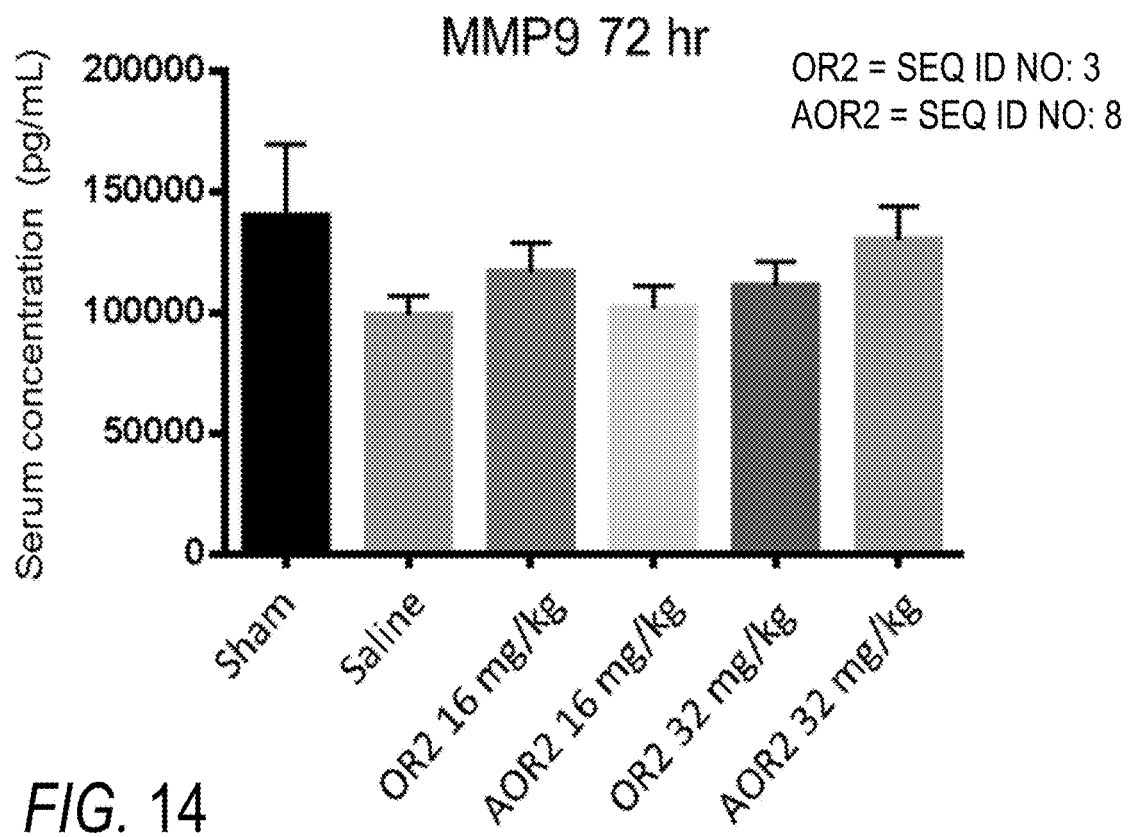
FIG. 14 is a bar graph of the MMP9 serum levels at 72 hours Data were analyzed relative to saline (no peptide) treatment using one-way ANOVA with Dunnett's post-hoc test. *p<0.05, **p<0.001.

Blood was drawn at 24 and 72 hours post-ICH. Serum was tested using ELISA to determine levels of MMP-9 (metalloproteinase-9) as a stroke biomarker. MMP9 serum levels are diminished 24 hours post-ICH with both SEQ ID NO:3 and SEQ ID NO: 8 treatment (32 mg/kg dose) showing protective efficacy of both peptides (FIG. 13). By 72 hours post-ICH, all animal groups had MMP9 levels that were not statistically different among the groups (FIG. 14).

This disclosure describes example aspects and embodiments, but not all possible aspects and embodiments. Where a particular feature is disclosed in the context of a particular aspect or embodiment, that feature can also be used, to the extent possible, in combination with and/or in the context of other aspects and embodiments. The composition and methods, be embodied in many different forms and should not be construed as limited to only the embodiments described here.

That which is claimed is:

1. A composition comprising at least one isolated amino acid sequence selected from SEQ ID NOs: 2, 3, 4, 5, and 6 in which at least one proline (P) residue in the amino acid sequence is substituted by an amino acid having the formula

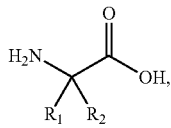

wherein R1 is a methyl group and R2 is an alkyl functional group having 1 to 4 carbon atoms.

2. The composition of claim 1, wherein R2 is selected from a methyl, ethyl, butyl, and propyl group.

3. The composition of claim 1, wherein R2 is a methyl group.

4. The composition of claim 1, wherein the composition is within a pharmaceutical dosage form.

5. A method of binding hemin, the method comprising administering to a hemin solution a composition comprising at least one isolated amino acid sequence selected from SEQ ID NOs: 2, 3, 4, 5, and 6 in which at least one proline (P) residue in the amino acid sequence is substituted by an amino acid having the formula

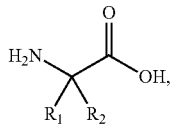

wherein R1 is a methyl group and R2 is an alkyl functional group having 1 to 4 carbon atoms; and wherein the isolated amino acid sequence is effective for binding to hemin in the hemin solution.

6. The method of claim 5, wherein R2 is selected from a methyl, ethyl, butyl, and propyl group.

7. The method of claim 5, wherein R2 is a methyl group.

8. The method of claim 5, wherein the composition is within a pharmaceutical dosage form.

9. A method of treating a hemorrhagic injury, the method comprising administering to a patient in need thereof a therapeutically effective composition comprising at least one isolated amino acid sequence selected from SEQ ID NOs: 2, 3, 4, 5, and 6 in which at least one proline (P) residue in the amino acid sequence is substituted by an amino acid having the formula

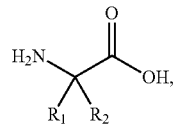

wherein R1 is a methyl group and R2 is an alkyl functional group having 1 to 4 carbon atoms.

10. The method of claim 9, wherein R2 is selected from a methyl, ethyl, butyl, and propyl group.

11. The method of claim 9, wherein R2 is a methyl group.

12. The method of claim 9, wherein the composition is within a pharmaceutical dosage form.

13. The method of claim 9, wherein the hemorrhagic injury is at least one hemorrhagic injury selected from the group consisting of stroke and traumatic brain injury.

* * * * *